US012685522B2

(12) United States Patent (10) Patent No.: US 12,685,522 B2
Curtis et al. (45) Date of Patent: Jul. 21, 2026

(54) SUTURE ANCHOR WITH MICROTHREADS AND SUTURE ANCHOR DRIVER WITH NEEDLE ATTACHMENT

(71) Applicant: AEVUMED, INC., Wayne, PA (US)

(72) Inventors: Miles Ole Curtis, Philadelphia, PA (US); Saif El Din Khalil, Wayne, PA (US); Joseph Albert Abboud, Bryn Mawr, PA (US); Peter Shay Johnston, Leonardtown, MD (US)

(73) Assignee: AEVUMED, INC., Malvern, PA (US)

( * ) Notice: Subject to any disclaimer, the term of this patent is extended or adjusted under 35 U.S.C. 154(b) by 229 days.

(21) Appl. No.: 15/780,910

(22) PCT Filed: Dec. 2, 2016

(86) PCT No.: PCT/US2016/064652
§ 371 (c)(1),
(2) Date: Jun. 1, 2018

(87) PCT Pub. No.: WO2017/096185
PCT Pub. Date: Jun. 8, 2017

(65) Prior Publication Data
US 2018/0360438 A1     Dec. 20, 2018

Related U.S. Application Data

(60) Provisional application No. 62/262,752, filed on Dec. 3, 2015.

(51) Int. Cl.
*A61B 17/04* (2006.01)
*A61F 2/08* (2006.01)
(Continued)

(52) U.S. Cl.
CPC ...... *A61B 17/0401* (2013.01); *A61B 17/0482* (2013.01); *A61F 2/0811* (2013.01);
(Continued)

(58) Field of Classification Search
CPC .......... A61B 17/0482; A61B 2017/044; A61B 17/0401; A61B 2017/00349;
(Continued)

(56) References Cited

U.S. PATENT DOCUMENTS 5,743,914 A * 4/1998 Skiba ................. A61B 17/8625
411/412
7,713,285 B1 * 5/2010 Stone ................. A61B 17/0401
606/232

(Continued)

*Primary Examiner* — Darwin P Erezo
*Assistant Examiner* — Christina C Lauer
(74) *Attorney, Agent, or Firm* — Riverside Law LLP

(57) ABSTRACT

A suture anchor is described. The suture anchor includes an elongate anchor body having a proximal end and a distal end, at least one suture secured within the anchor body, at least one major thread, and at least two microthreads occupying the space between each major thread. An anchor driver is also described. The anchor driver is capable of accepting various attachments such that an operator can change the functionality of the driver based on the type of attachment in use, such as a needle attachment. A method of attaching soft tissue to bone in a subject is also described. The method includes the steps of securing a suture anchor into bone with the anchor driver, joining a needle attachment with the anchor driver, passing at least one suture through soft tissue using the needle attachment, and tying the at least one suture against the soft tissue to secure the soft tissue to the bone.

23 Claims, 13 Drawing Sheets

(51) Int. Cl.
    *A61B 17/00*            (2006.01)
    *A61B 17/06*            (2006.01)

(52) U.S. Cl.
    CPC .............. *A61B 2017/00349* (2013.01); *A61B 2017/00477* (2013.01); *A61B 2017/0409* (2013.01); *A61B 2017/0414* (2013.01); *A61B 2017/044* (2013.01); *A61B 2017/0441* (2013.01); *A61B 2017/0445* (2013.01); *A61B 2017/0448* (2013.01); *A61B 2017/0464* (2013.01); *A61B 2017/06019* (2013.01); *A61B 2017/0608* (2013.01); *A61F 2002/0841* (2013.01)

(58) Field of Classification Search
    CPC .. A61B 2017/00477; A61B 2017/0409; A61B 2017/0414; A61B 2017/0441; A61B 2017/0445; A61B 2017/0448; A61B 2017/0464; A61B 2017/06019; A61B 2017/0608; A61B 2/0811; A61B 2002/0841

USPC ........................................................ 606/232
    See application file for complete search history.

(56)                    References Cited

U.S. PATENT DOCUMENTS

| | | | |
|---|---|---|---|
| 9,055,986 B1 * | 6/2015 | Whipple ............ | A61B 17/8625 |
| 2004/0082956 A1 * | 4/2004 | Baldwin ............ | A61B 17/0401 |
| | | | 606/232 |
| 2009/0234387 A1 * | 9/2009 | Miller ................ | A61B 17/0401 |
| | | | 606/232 |
| 2014/0081325 A1 * | 3/2014 | Sengun .............. | A61B 17/0469 |
| | | | 606/232 |
| 2014/0228880 A1 * | 8/2014 | Bisson .............. | A61B 17/0401 |
| | | | 606/232 |
| 2014/0277139 A1 * | 9/2014 | Vrionis ................ | A61F 2/4455 |
| | | | 606/246 |
| 2015/0230844 A1 * | 8/2015 | Ellis .................. | A61B 17/8635 |
| | | | 606/316 |
| 2016/0015483 A1 * | 1/2016 | Kumar ................ | A61C 8/0075 |
| | | | 606/301 |

* cited by examiner

31

34

32

36

30

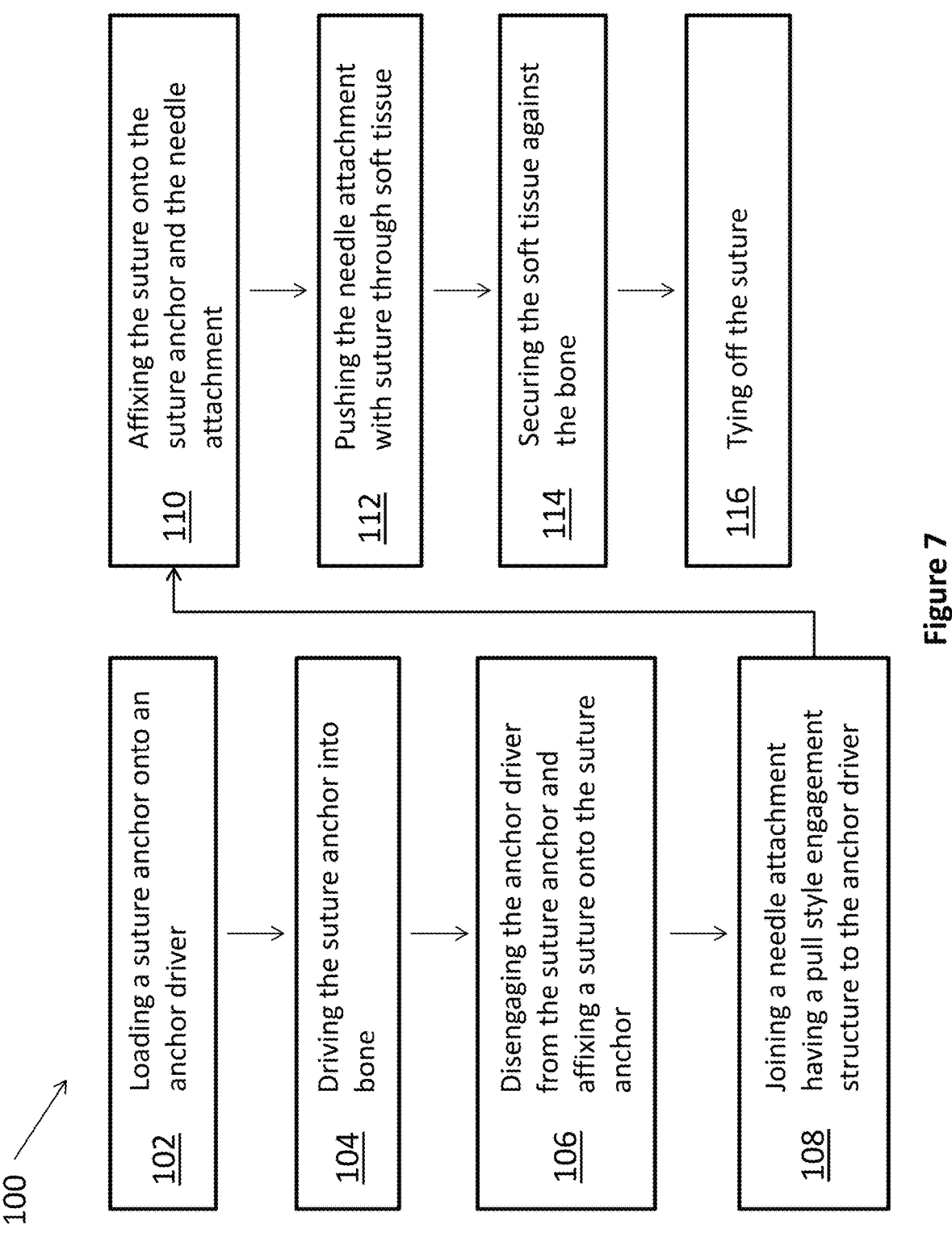

100

102 Loading a suture anchor onto an anchor driver

104 Driving the suture anchor into bone

106 Disengaging the anchor driver from the suture anchor and affixing a suture onto the suture anchor 108 Joining a needle attachment having a pull style engagement structure to the anchor driver 110 Affixing the suture onto the suture anchor and the needle attachment 112 Pushing the needle attachment with suture through soft tissue 114 Securing the soft tissue against the bone 116 Tying off the suture

Figure 7

SUTURE ANCHOR WITH MICROTHREADS AND SUTURE ANCHOR DRIVER WITH NEEDLE ATTACHMENT

CROSS-REFERENCE TO RELATED APPLICATIONS

This application is a U.S. national phase application filed under 35 U.S.C. § 371 claiming benefit to International Patent Application No. PCT/US16/64652, filed Dec. 2, 2016, which is entitled to priority under 35 U.S.C. § 119 (e) to U.S. Provisional Patent Application No. 62/262,752, filed Dec. 3, 2015, the contents of which are each incorporated herein by reference in their entirety.

BACKGROUND OF THE INVENTION

The attachment of soft tissue to bone remains an important part of the practice of orthopedic surgery. The surgeon's armamentarium for attaching ligaments, tendons, or other tissues to bone includes pullout suture techniques, keyhole techniques, smooth or barbed soft tissue staples, and fixation with screws and washers. Each of these devices and techniques has advantages and disadvantages, depending on the surgical situation and the clinical application. The development of suture anchors, which has revolutionized soft tissue fixation to bone, has paralleled the development of arthroscopic surgical techniques. Suture anchors have been used successfully for rotator cuff repairs, shoulder reconstructions for instability, the repair of biceps anchor lesions (e.g., superior labrum anterior posterior (SLAP) lesions), and biceps tenodesis. The continuing evolution of suture anchors has produced a variety of types, such as absorbable, non-absorbable, screw-in, hooked, and knotless anchors and tacks, as well as those that lock into the bone on insertion.

Traditionally, the suture attachment to the soft tissue is secured via a knot made in the suture. In order to convey this type of procedure, a number of steps are required to complete this process. This process is as follows; 1) the bone is bored out and the suture anchor is deployed and secured in to the bone; 2) a surgical instrument or device such as a lasso is inserted through a second surgical port and pierces through the soft tissue; 3) a looped end wire is pushed out of the tip of the surgical instrument or device; 4) the looped end wire is then pulled out of the first suture anchor insertion port using a grasper; 5) one of the sutures is passed through the looped end wire out of the first suture anchor insertion port; 6) the looped end wire is then pulled back out of the second surgical port and sequentially pulls the suture out of the second surgical port; 7) a grasper is then inserted through the first suture anchor insertion port and pulls the suture back out of the first suture anchor insertion port; and 8) the two suture ends are then tied out of the first suture anchor insertion port and pushed down to secure the soft tissue to bone.

However, there is a clinical need for a less invasive method to reduce the number of steps and operating time in soft tissue fixation to bone, as well as reduce the risk of infection. Unfortunately, existing designs require too many steps, have relatively long operating times, and require a surgical instrument or device such as a lasso to pass a suture end through soft tissue.

For example, U.S. Pat. No. 5,697,950 describes a method and apparatus for facilitating use of a threaded suture anchor in combination with a cannulated anchor driver. The device enables a suture anchor to be preassembled with a suture so that a user need not assemble a suture anchor with suture immediately prior to use. Similarly, U.S. Pat. No. 5,993,459 describes a method and suture anchor installation system that includes a suture anchor, a loading unit, and a suture anchor installation tool. However, these methods require the use of an external instrument to pass the suture through tissue.

U.S. Pat. No. 7,875,042 describes a suture anchor loader comprises a housing with a port. On the other hand, U.S. Patent Application Publication No. 2010/0268274 describes a suture anchor member manual loading device that may include a body comprising first and second portions preventing the operator contact with a tip of a needle. In addition, U.S. Patent Application Publication No. 2011/0071551 describes a soft tissue repair system that includes a sheath, and an actuator. However, all these methods still require the use of an external instrument to pass the suture through tissue. This greatly increases the time, complexity, and risk during the fixation procedure.

Thus, there is a need in the art for an improved device and method for the attachment of soft tissue to bone to reduce the number of steps required for effective fixation. The present invention satisfies this unmet need.

SUMMARY OF THE INVENTION

The present invention relates to devices and methods for attaching soft tissue to bone. The invention also relates to a suture anchor driver capable of accepting different attachments for use in attaching soft tissue to bone. The invention reduces the number of surgical entry points required by providing an anchor driver having a plurality of functionalities to enter a single surgical entry point.

In one aspect, the invention is a suture anchor comprising: an elongate anchor body having a proximal end and a distal end; at least one major thread covering the length of the anchor body; and at least two microthreads covering the length of the anchor body, wherein the at least two microthreads occupy the space between the at least one major thread, and wherein the at least two microthreads have major diameters that are smaller than the major diameters of the at least one major thread.

In one embodiment, the suture anchor further comprises at least one suture secured to the anchor body. In one embodiment, the proximal end of the anchor body comprises a channel for engagement with an installation tool. In one embodiment, the at least one suture is secured within the channel of the anchor body. In one embodiment, the at least two microthreads have the same major diameter. In one embodiment, the at least two microthreads have different major diameters. In one embodiment, the major diameter of the at least one major thread, the at least two microthreads, or both is variable. In one embodiment, the distal end of the anchor body comprises one or more cutting flutes. In one embodiment, the distal end of the anchor body comprises a self-drilling tip.

In another aspect, the invention is an anchor driver comprising: an elongate shaft having a proximal end and a distal end; a driving bit at the distal end of the shaft; an attachment feature positioned between the driving bit and the shaft; and a cannula extending through the entire length of the anchor driver.

In one embodiment, the cannula is accessible by a channel running along the entire length of the anchor driver. In one embodiment, the cannula is dimensioned to fit at least one suture. In one embodiment, the attachment feature is selected from the group consisting of: a thread, a detent, a latch, a snap fit mechanism, and an interference/friction fit mechanism. In one embodiment, the attachment feature is a rotating sheath having a thread, a tab and slot mechanism, a notch mechanism, or a clamp and jaw mechanism.

In another aspect, the invention is a needle attachment comprising: a grip comprising an engagement feature; an elongate stem; a needle tip; and an engagement structure. In one embodiment, the grip engagement feature is selected from the group consisting of: a thread, a detent, a latch, a snap fit mechanism, and an interference/friction fit mechanism. In one embodiment, the engagement structure is selected from the group consisting of: a hole, a slot, a crimp, a barb, and a notch. In one embodiment, the engagement structure is a pull type engagement structure that holds a suture as the needle attachment is pulled through soft tissue. In one embodiment, the engagement structure is a push type engagement structure that holds a suture as the needle attachment is pushed through soft tissue. In one embodiment, the elongate stem comprises one or more curves or bends. In one embodiment, the needle attachment further comprises an occluding structure to prevent the engagement structure from catching onto tissue. In one embodiment, the occluding structure is a movable sleeve or latch. In one embodiment, the elongate stem comprises a lumen, wherein the needle tip and engagement structure are movable within the lumen, and wherein the needle tip can be deployed to expose the engagement structure and retracted to hide the engagement structure. In one embodiment, the needle tip is split into two hinged halves actuatable about a hinge. In one embodiment, each hinged half comprises an extension near the hinge.

In another aspect, the invention is a method of attaching soft tissue to bone in a subject using a needle attachment having a push style engagement structure, the method comprising the steps of: loading a suture anchor onto an anchor driver; driving the suture anchor into a bone; disengaging the anchor driver from the suture anchor and affixing a suture onto the suture anchor; joining a needle attachment having a push style engagement structure to the anchor driver; affixing a suture onto the needle attachment; passing the needle attachment with suture through soft tissue; securing the soft tissue against the bone; and tying off the suture.

In another aspect, the invention is a method of attaching soft tissue to bone in a subject using a needle attachment having a pull style engagement structure, the method comprising the steps of: loading a suture anchor onto an anchor driver; driving the suture anchor into a bone; disengaging the anchor driver from the suture anchor and affixing a suture onto the suture anchor; joining a needle attachment having a pull style engagement structure to the anchor driver; pushing the needle attachment through soft tissue; affixing a suture onto the needle attachment; pulling the needle attachment with suture through soft tissue; securing the soft tissue against the bone; and tying off the suture.

In one embodiment, an anchor driver with a preloaded suture anchor is used. In one embodiment, the suture anchor is preloaded with a suture. In one embodiment, the suture anchor is secured into the bone through self-drilling. In one embodiment, the suture anchor is secured into the bone by forming a bore in the bone using a bore-forming tool, and securing the suture anchor into the bore. In one embodiment, the soft tissue is selected from the group consisting of: tendon, muscle, and ligament.

In another aspect, the invention is a system for attaching soft tissue to bone in a subject, the system comprising: a suture anchor comprising an elongate anchor body having a proximal end and a distal end, at least one suture secured to the anchor body; at least one major thread covering the length of the anchor body; and at least two microthreads covering the length of the anchor body; an anchor driver comprising an elongate shaft having a proximal end and a distal end; a driving bit at the distal end of the shaft; an attachment feature positioned between the driving bit and the shaft; and a cannula extending through the entire length of the anchor driver; and a needle attachment comprising a grip having an engagement feature complementary to the attachment feature of the anchor driver; an elongate stem; a needle tip; and an engagement structure. In one embodiment, the system further comprises a plurality of attachments selected from the group consisting of: tissue manipulator attachments, bore forming attachments, and bore tapping attachments.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 7 is a flowchart illustrating an exemplary method for securing soft tissue to bone using the devices of the present invention and a needle attachment having a push style engagement structure.

DETAILED DESCRIPTION

Figure 1:
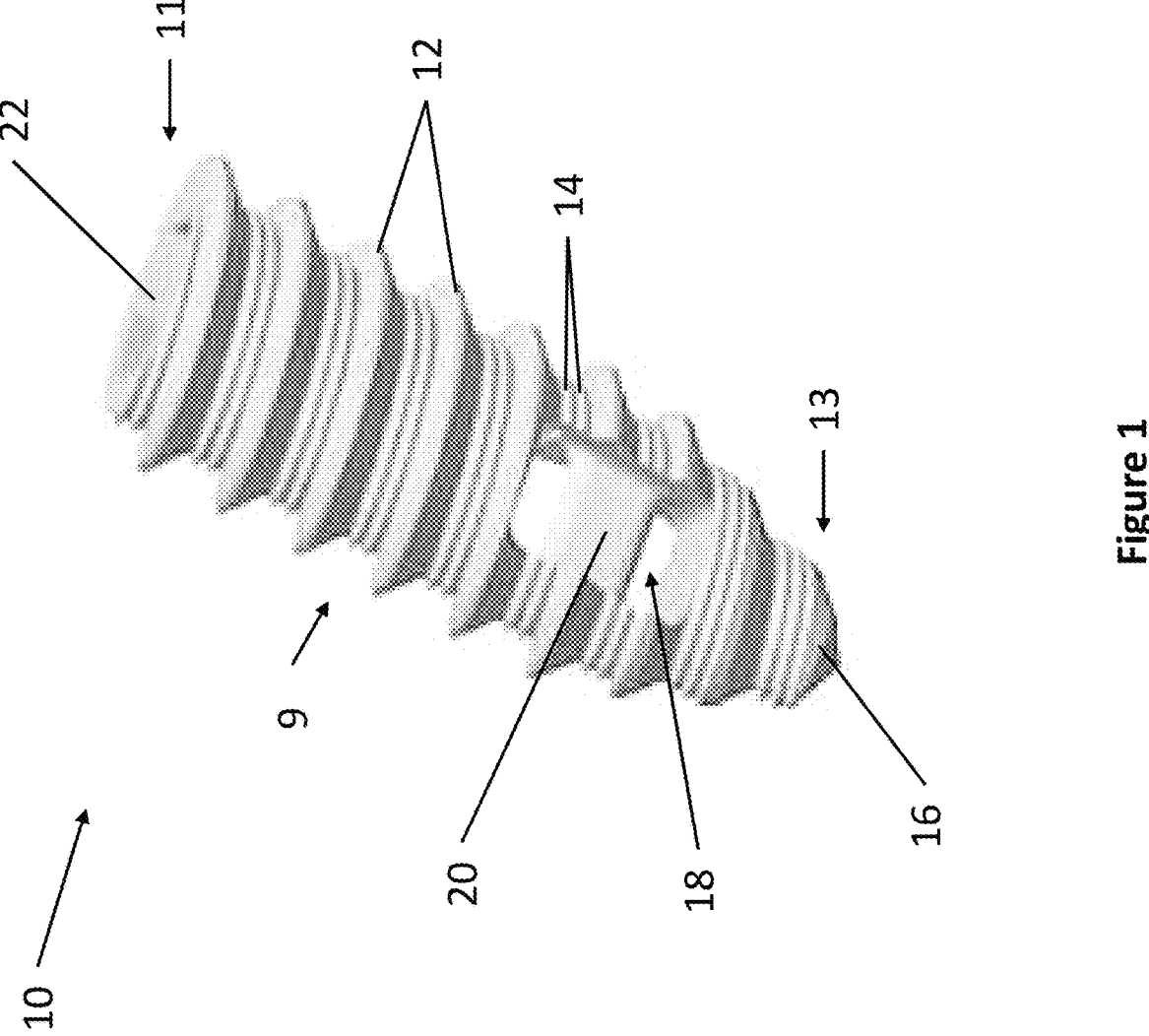
FIG. 1 is a perspective view of an exemplary suture anchor.

The present invention relates to devices and methods for attaching soft tissue to bone. The invention relates to a suture anchor having microthreads. The invention also relates to a suture anchor driver capable of accepting different attachments, including a needle attachment. The invention also relates to methods of using the suture anchor having microthreads and the suture anchor driver with needle attachment.

In situations where ligaments or other soft tissue are being sutured to bone, a suture anchor is commonly employed. The suture anchor is inserted into a bore hole in the bone and a suture extending from the anchor is attached to the soft tissue to be secured to the bone. The present invention improves upon this clinical procedure by improving the pullout strength of the suture anchor and by reducing the amount of steps required for efficient fixation.

As described herein, the design of the suture anchor of the present invention increases the pullout strength of the suture anchor after being driven into bone. The suture anchor comprises microthreads that enhance grip on hard tissue. The design of the suture anchor driver with needle attachment reduces the number of traditional steps required to attach soft tissue to bone. A needle attachment can be joined to the suture anchor driver to pass sutures through soft tissue, which eliminates the need for sets of separate instruments.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

As used herein, the term "crest" refers to the portion of a screw which is farthest from the body of the screw and which is defined by the flanks of the thread.

"Hard tissue" as used herein refers to mineralized tissues, such as bone.

As used herein, the term "lead" refers to the distance a screw thread advances axially in one complete rotation of a thread.

As used herein, the term "major diameter" refers to the diameter at the crest of a screw.

As used herein, the term "minor diameter" refers to the diameter at the root of a screw.

As used herein, the term "pitch" refers to the distance from the crest of one thread to the next.

As used herein, the term "root" refers to the narrow inner surface between the threads of a screw.

As used herein, the term "secured," "anchored," "held," "fastened" and similar terms refer to a first component or part being at least temporarily secured, anchored, held, fastened or the like, to a second component or part. In other words, any component described as being secured, anchored, held or fastened to a another component may be either releasably or permanently secured, anchored, held or fastened, unless specifically described otherwise.

"Soft tissue" as used herein refers to tissues such as, without limitation, tendons, ligaments, fascia, skin, muscle, fibrous tissues, nerves, blood vessels, synovial membranes and fat.

As used herein, the term "thread" refers to the helical protruding portion of a screw which engages or displaces surrounding material (e.g., bone) with which the screw comes in contact.

As used herein, the term "taper" or "tapered" refers to an elongated structure with a gradual diminution of width or thickness.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Suture Anchor Having Microthreads

The present invention relates to a suture anchor for attaching a soft, first tissue to a hard, second tissue. For example, in certain embodiments, the suture anchor is used to attach a soft tissue including, but not limited to, a ligament, tendon, muscle, and the like, to a hard tissue such as bone. As described herein, the suture anchor of the invention comprises one or more microthreads which enhance the pullout strength of the suture anchor. In one embodiment, one or more microthreads occupy the space between the suture anchor's major threads.

As shown in FIG. 1, an exemplary suture anchor 10 of the present invention comprises an elongate anchor body 9 having a proximal end 11 and a distal end 13. Suture anchor 10 may be manufactured from any suitable biocompatible material known in the art, including, but not limited to: titanium, titanium alloys, stainless steel, Nitinol, polyether-ether-ketone (PEEK), cobalt, alloys thereof, biodegradable polymers, non-degradable polymers, polymeric materials such as non-absorbable polyesters, polyamides, polyolefins, polyurethanes, and polyacetals, homopolymers and copolymers of lactide, glycolide, trimethylene carbonate, caprolactone, and p-dioxanone and blends or and any combinations thereof. In certain embodiments, suture anchor 10 is made of a bioabsorbable material and does not need to be removed from the bone. In one embodiment, suture anchor 10 is made of a non-absorbable material.

Suture anchor 10 may be of any size suitable for the particular application for which it is used. In one embodiment, anchor body 9 has a length of about 1 mm to about 200 mm. In another embodiment, anchor body 9 has a length of about 3 mm to about 100 mm. The outer surface of anchor body 9 comprises major thread 12 and microthreads 14. In one embodiment, suture anchor 10 comprises one or more major thread 12. In one embodiment, suture anchor 10 comprises one or more microthread 14 disposed between major thread 12. In various embodiments, suture anchor 10 comprises two, three, four, five, or more microthreads 14. Major thread 12 can have any suitable major diameter. For example, major thread 12 can have a major diameter between 2 mm and 10 mm. Microthreads 14 can have any suitable major diameter. For example, microthreads 14 can have a major diameter between 1 mm and 9 mm. In some embodiments, a plurality of microthreads 14 has the same major diameter. In other embodiments, a plurality of microthreads 14 has different major diameters. In various embodiments, major thread 12, microthread 14, or both have variable major diameters. Suture anchor 10 can have any suitable pitch, or spacing between each thread. For example, suture anchor 10 can have a pitch between 0.1 mm and 5 mm.

In one embodiment, proximal end 11 comprises driver socket 22 for engaging an installation tool. For example, driver socket 22 is a channel that may have a cross-sectional geometry of a circle, oval, triangle, rectangle, polygon, hexagon, irregular shape, or the like. Driver socket 22 is configured to engage a male driver bit of an installation tool to aid in the installation of suture anchor 10. Driver socket 22 extends through anchor body 9 and terminates in aperture 18. Aperture 18 is located adjacent to distal end 13 and runs through suture anchor 10 laterally. Aperture 18 provides access to rod 20, which extends across the space of aperture 18.

Driver socket 22 and rod 20 are arranged such that a length of suture thread is secured to suture anchor 10 by passing into driver socket 22 at proximal end 11, looping around rod 20, and passing out of driver socket 22 at proximal end 11. Aperture 18 is provided to facilitate looping a length of suture thread around rod 20. In certain embodiments, suture anchor 10 comprises more than one suture. For example, in one embodiment, more than one suture is positioned within driver socket 22. In certain embodiments, the suture, when loaded into suture anchor 10, is free to move (e.g., slide or slip) within driver socket 22. In another embodiment, the suture, when loaded into suture anchor 10, is substantially non-movable, thereby securing the suture to suture anchor 10. The suture may be any suture known in the art suitable for the particular application. Exemplary sutures include sutures made from materials including, but not limited to, catgut, silk, linen, nylon, polyglycolic acid, polyglactin, polydioxone, polyglyconate, polyamide, polyester, polypropylene, polyethylene, and ultra-high molecular weight polyethylene.

At least a portion of the outer surface of anchor body 9 engages a bone, for example through a hole formed in the bone using a bore-forming tool such as a drill, awl, tap, and the like. In one embodiment, the engaging portion of anchor body 9 extending proximally from distal end 13 is substantially cylindrical, thereby having a substantially constant diameter. In another embodiment, a portion of anchor body 9 is tapered. For example, in one embodiment, at least the distal portion of anchor body 9 is tapered. In one embodiment, the engaging portion of anchor body 9 has a cylindrical region and a tapered region. Distal end 13 comprises distal tip 16. In various embodiments, distal tip 16, distal end 13, or both may include one or more self-tapping cutting flutes, or otherwise form a self-drilling tip.

Suture Anchor Driver

The present invention relates to an anchor driver for driving bone anchors, such as the suture anchor of the present invention. The anchor driver is capable of accepting various attachments such that an operator can change the functionality of the driver based on the type of attachment in use. The anchor driver reduces the number of surgical entry points required by providing an anchor driver having a plurality of functionalities to enter a single surgical entry point.

Figure 2:
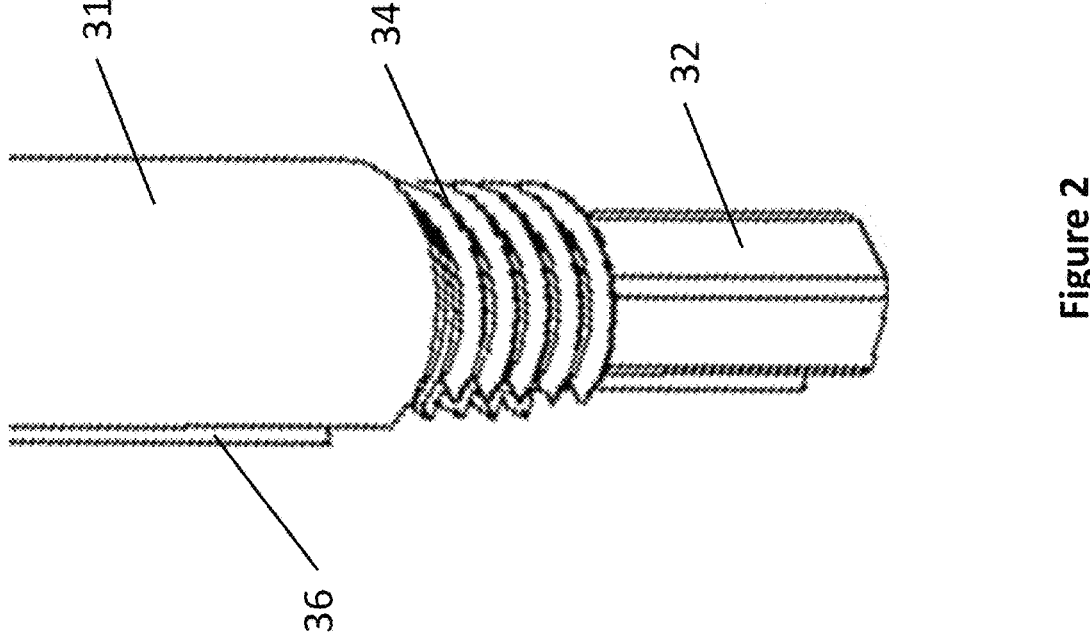
FIG. 2 is a perspective view of an exemplary anchor driver tip for use with the suture anchor of FIG. 1.

Referring now to FIG. 2, the distal tip of an exemplary anchor driver 30 is depicted. Anchor driver 30 comprises shaft 31, suture channel 36, attachment thread 34, and driving bit 32. Anchor driver 30 may further comprise other features common to drivers in the art, such as a handle or a grip at its proximal end (not pictured).

In one embodiment, anchor driver 30 is cannulated. For example, anchor driver 30 may have a cannula for accommodating at least one suture thread. In one embodiment, suture channel 36 comprises a depth that reaches the cannula. In various embodiments, suture channel 36 has a width of 1 mm to 3 mm. Suture channel 36 runs through the entire length of shaft 31, attachment thread 34, and driving bit 32.

Anchor driver 30 comprises driving bit 32 at its distal tip. Driving bit 32 can comprise any geometric configuration suitable for mating and engaging with a screw, as would be understood by those skilled in the art. In one embodiment, driving bit 32 comprises a geometric configuration suitable for mating and engaging with a suture anchor, as described elsewhere herein. In one embodiment, driving bit 32 may have a cross-sectional geometry of a circle, oval, triangle, rectangle, polygon, hexagon, irregular shape, or the like.

Situated between shaft 31 and driving bit 32 is attachment thread 34. Attachment thread 34 is dimensioned such that any number of attachments may be joined to the distal end of anchor driver 30. In one embodiment, attachment thread 34 may be a machine style thread. In one embodiment, attachment thread 34 may be a male thread. In one embodiment, attachment thread 34 has a minor diameter that is larger than the diameter of driving bit 32. In one embodiment, attachment thread 34 has a major diameter that is smaller than the diameter of shaft 31.

In certain embodiments, anchor driver 30 can comprise any sort of temporary securing system known in the art, such as a detent, latch, snap fit mechanism, or interference/friction fit mechanism. The temporary securing system permits an attachment to be joined to the distal end of anchor driver 30, then subsequently released from the distal end of anchor driver 30 with the application of a light, pulling force. In some embodiments, the temporary securing system further comprises a keyed or notched geometry, such that an attachment joined to the distal end of anchor driver 30 is unable to rotate (not pictured).

In some embodiments, the temporary securing system comprises a rotating sheath located on the exterior of shaft 31 at its distal end (not pictured). The sheath is able to free rotate to engage an attachment joined to the distal end of anchor driver 30. For example, the sheath can comprise an external or an internal attachment thread to secure an attachment without rotating the attachment or anchor driver 30. In one embodiment, the attachment thread is a timed thread, such that when an attachment is fully threaded to the distal end of anchor driver 30, the sheath is reliably oriented. A timed thread is advantageous to align a feature of the sheath with a feature of an attachment, a feature of anchor driver 30, or both. For example, a timed thread can reliably align a slot or notch on the sheath with suture channel 36 of anchor driver 30. In another example, the sheath can comprise a tab and slot mechanism, a notch mechanism, a clamp and jaw mechanism, or any other suitable engaging mechanism to securely fasten an attachment to anchor driver 30. In certain embodiments, the sheath comprises texturing to improve grip during rotation.

In various embodiments, anchor driver 30 is capable of accepting various attachments at its distal end such that an operator can change the functionality of the anchor driver based on the type of attachment in use. Non-limiting examples of attachments include, but are not limited to: needle attachments, trocar attachments, tissue manipulator attachments, bore forming attachments, bore tapping attachments, and the like.

Needle Attachments

The present invention relates to needle attachments for use with the anchor driver of the present invention. The needle attachments, when joined to the distal end of the anchor driver, provide the anchor driver with the functionality of passing sutures through soft tissue.

Figure 3:
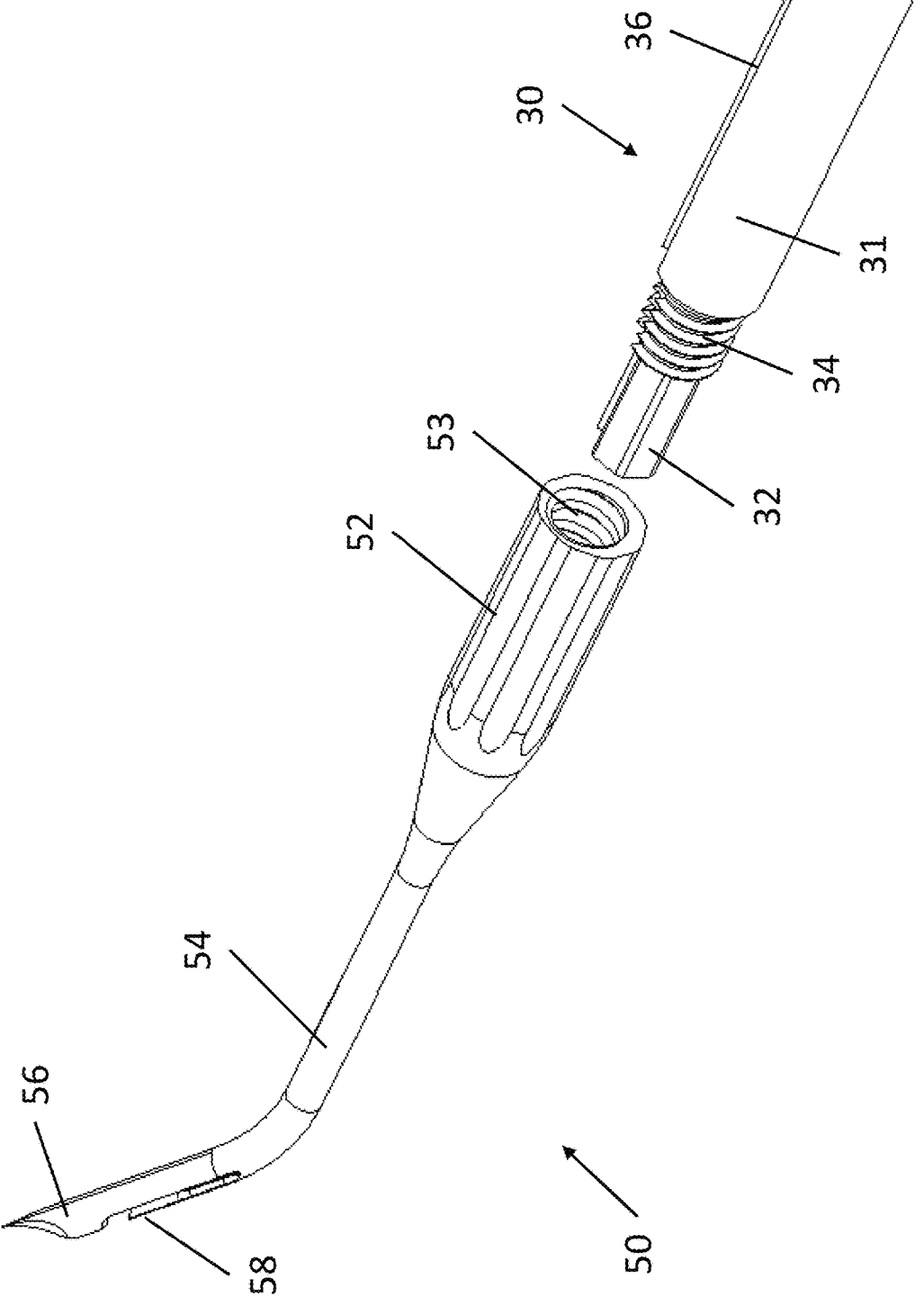
FIG. 3 is a perspective view of an exemplary needle attachment.

Referring now to FIG. 3, an exemplary needle attachment 50 is depicted.

Figure 4:
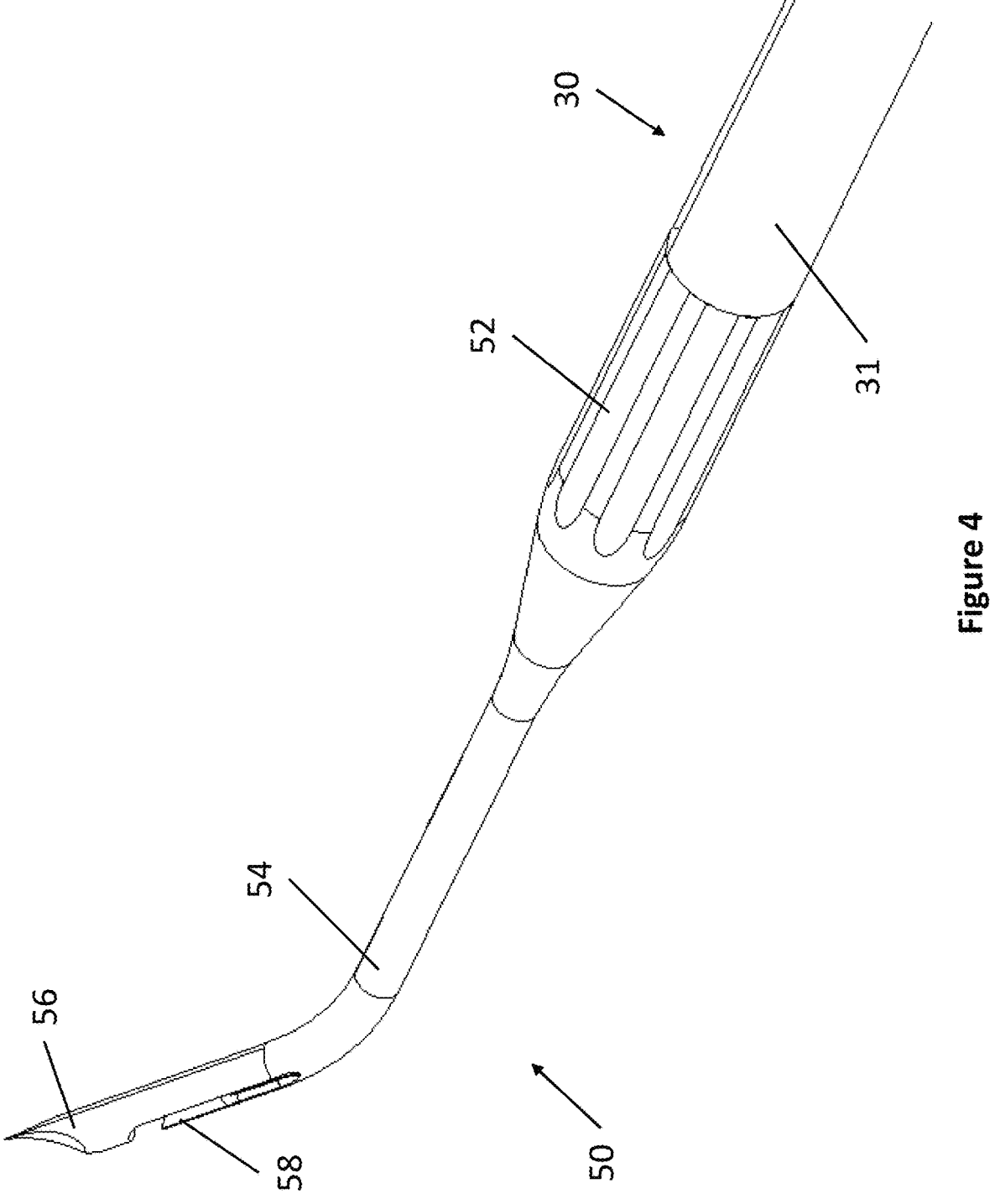
FIG. 4 is a perspective view of the exemplary needle attachment of FIG. 3 attached to the exemplary anchor driver of FIG. 2.
Figure 6:
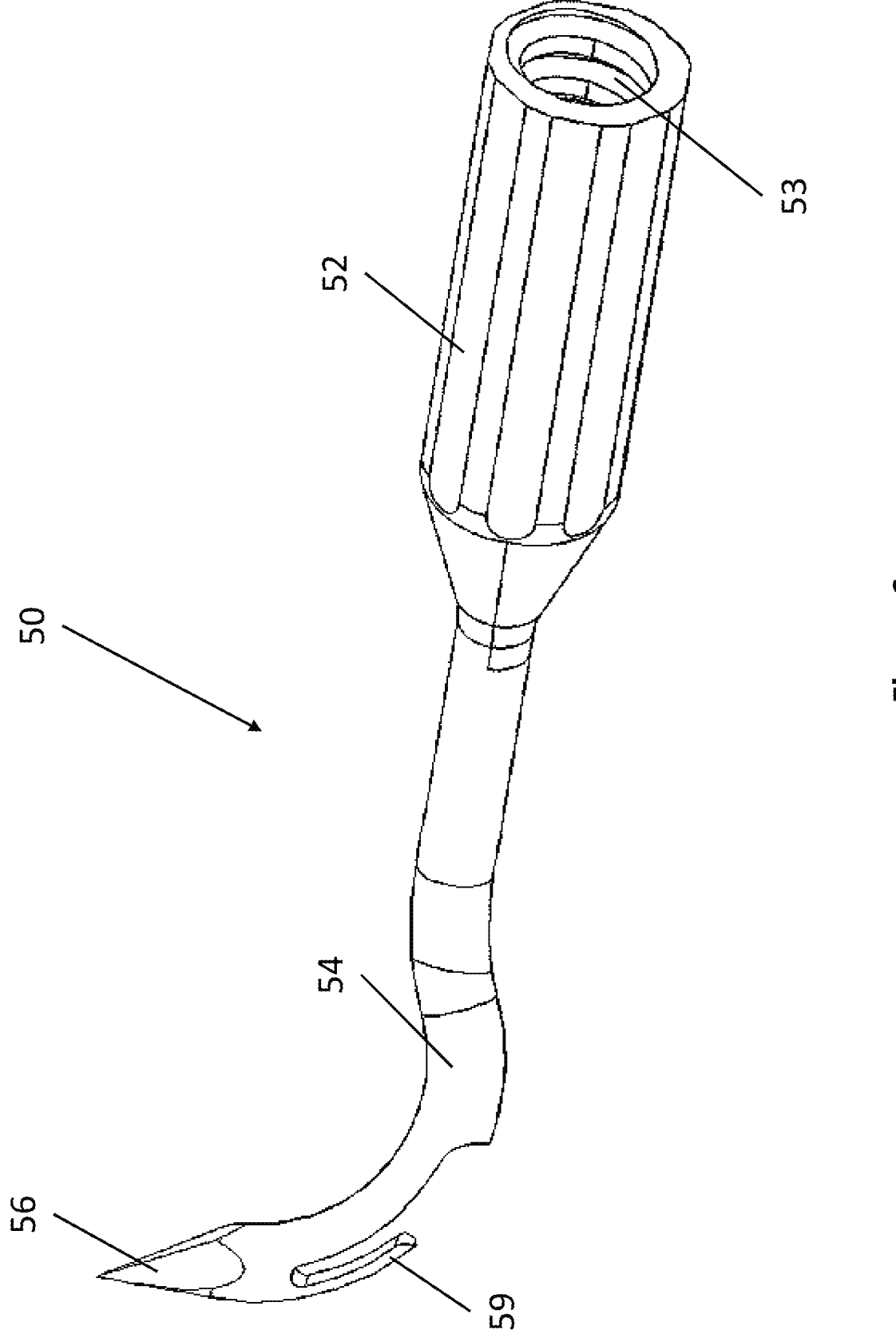
FIG. 6 is a perspective view of an exemplary needle attachment having a pull style engagement structure.

Needle attachment 50 comprises grip 52, stem 54, and needle tip 56. Grip 52 comprises grip thread 53. Needle tip 56 comprises push style engagement structure 58. In some embodiments, needle tip 56 comprises pull style engagement structure 59 (FIG. 6). Needle attachment 50 may be joined to the distal end of suture anchor driver 30, as depicted in FIG. 4.

Needle attachment 50 comprises grip 52 at its proximal end. Grip 52 may comprise ridges, grooves, or any other suitable texture to enhance an operator's hold on needle attachment 50. Grip 52 comprises internal grip thread 53 that is capable of mating and engaging with attachment thread 34 of anchor driver 30. In certain embodiments, instead of an internal thread, needle attachment 50 comprises any sort of temporary securing system known in the art, such as a detent, latch, snap fit mechanism, or interference/friction fit mechanism, to permit needle attachment 50 to be secured to the distal end of anchor driver 30, then subsequently released from the distal end of anchor driver 30 with the application of a light, pulling force. In some embodiments, the temporary securing system further comprises a keyed or notched geometry, such that a needle attachment 50 joined to the distal end of anchor driver 30 is unable to rotate (not pictured).

Stem 54 extends distally from grip 52. In some embodiments, stem 54 comprises a substantially circular cross section, such that stem 54 has a rod-like shape. In some embodiments, stem 54 comprises a lumen running throughout, such that stem 54 has a tube-like shape (not pictured). Stem 54 may have any suitable length. For example, stem 54 may have a length between 0.1 mm to about 50 mm. In some embodiments, stem 54 is substantially straight. In other embodiments, stem 54 comprises one or more bend, twist, or any other nonlinear shape that may be useful to direct and pass a suture through soft tissue. Stem 54 may be manufactured from any suitable substantially rigid material, such as titanium or stainless steel.

Needle tip 56 tapers to form a piercing tip at the leading distal end of needle attachment 50. In some embodiments needle tip 56 is a trocar tip. In some embodiments, needle tip 56 comprises a variable diameter tip that tapers distally, such as in the shape of a cone (not pictured). Needle tip 56 is suitable for piercing, for example, a targeted soft tissue. Needle tip 56 may be of any length extending from the distal end of stem 54. For example, the length of needle tip 56 extending from the distal end of stem 54 can be any suitable length that traverses the entirety of the thickness of the soft tissue being secured to bone. In one embodiment, the length of needle tip 56 extending from the distal end of stem 54 is between about 0.1 mm to about 50 mm. Needle tip 56 may be manufactured from any suitable substantially rigid material, such as titanium or stainless steel.

Figure 5:
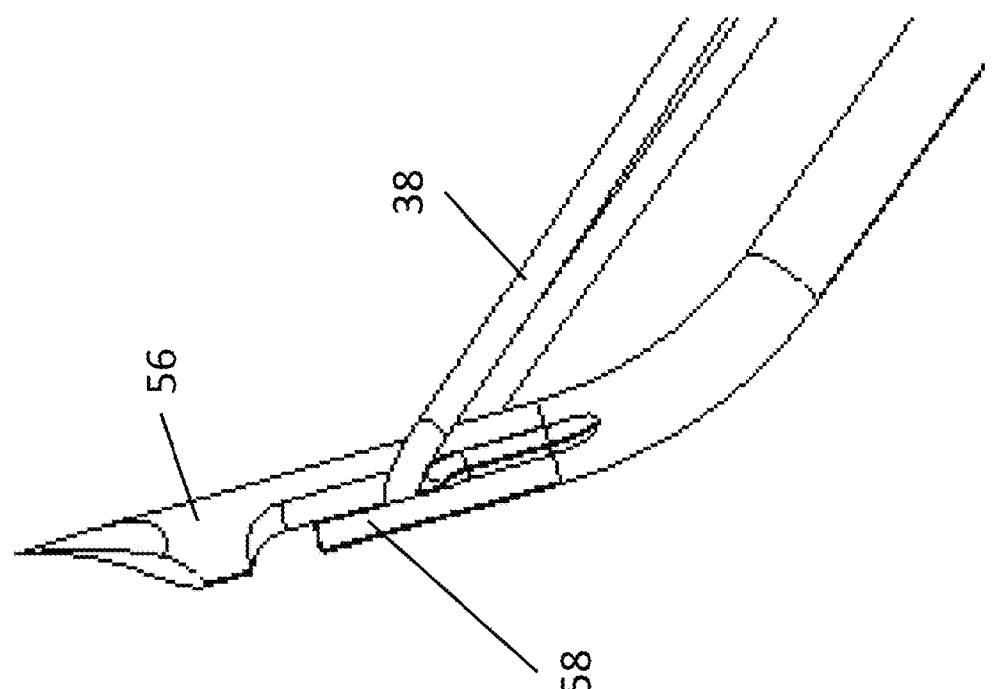
FIG. 5 is a perspective view of the needle tip of the exemplary needle attachment of FIG. 3 with a suture affixed to the needle tip via a push style engagement structure.

Needle tip 56 comprises at least one push style engagement structure 58 for engaging one or more sutures. Push style engagement structure 58 is structured such that the engagement structure maintains a hold on a suture as the needle attachment is pushed through a medium, such as soft tissue. In some embodiments, needle tip 56 comprises at least one pull style engagement structure 59 for engaging one or more sutures (FIG. 6). Pull style engagement structure 59 is structured such that the engagement structure maintains a hold on a suture as the needle attachment is pulled through a medium, such as soft tissue. In certain embodiments, a needle attachment may comprise at least one engagement structure having both a push style and a pull style engagement structure. Exemplary engagement structures may be, without limitation, a hole, slot, crimp, notch, barb, and the like. For example, as depicted in FIG. 5, needle tip 56 comprises at least one push style engagement structure 58 configured to engage at least a portion of a suture, such that the suture can be pushed through soft tissue along with needle tip 56. In another example, as depicted in FIG. 6, needle tip comprises at least one pull style engagement structure 59 configured to engage at least a portion of a suture, such that the suture can be pulled through soft tissue along with needle tip 56. In various embodiments, the engagement structure further comprises an occluding structure to prevent the engagement structure from unintentionally catching onto tissue as needle tip 56 is moved in and out of tissue (not pictured). In some embodiments, the occluding structure is a protective sleeve that slips over the engagement structure before or after the engagement structure engages a suture thread. In some embodiments, the occluding structure is a latch. The latch can be actuated about a hinge mechanism or by a spring-loaded mechanism to close the gap of an engagement structure or to cover an edged engagement structure to prevent the engagement structure from catching onto tissue.

In some embodiments, needle tip 56 comprises two halves joined together at a proximal hinge and ending in a distal piercing tip (not pictured). The two hinged halves are capable of opening and closing, such that when the two hinged halves are open, needle tip 56 is split down the center, and when the two hinged halves are closed, needle tip 56 forms a single piercing structure. The two hinged halves can open to accept a suture thread, then close to firmly grasp the suture thread. In some embodiments, the two hinged halves can be opened and closed by a spring-loaded mechanism. The spring-loaded mechanism can be biased to keep the two hinged halves open, or the spring-loaded mechanism can be biased to keep the two hinged halves closed. The spring-loaded mechanism can be connected to an actuator to actuate against the bias to control the opening and closing of the two hinged halves. In some embodiments, the two hinged halves each comprise a small extension near the hinge. The extensions enable the opening and closing of the two hinged halves to be driven by movement of needle tip 56 through tissue. For example, a closed needle tip 56 can cleanly pierce and penetrate tissue through a small entry point. Further penetration into the tissue will cause the extensions to press against the tissue, whereupon additional penetration will cause the tissue to push the extensions and force the two hinged halves to split apart and open away from each other. Withdrawing needle tip 56 from the tissue will release the extensions from the tissue, and the two hinged halves will close due to the small entry point in the tissue made by needle tip 56.

In some embodiments, needle tip 56 and an engagement structure is movable within the lumen of a tube-like stem 54 (not pictured). For example, needle tip 56 can protrude from the distal end of a tube-like stem 54 while the engagement structure of needle tip 56 is housed within the lumen of the tube-like stem 54. Needle tip 56 is thereby able to penetrate tissue without the risk of the engagement structure catching onto tissue. To engage a suture thread, needle tip 56 can be deployed distally to expose the engagement structure at the distal end of the tube-like stem 54. Upon engaging the suture thread, needle tip 56 can be retracted proximally to position the engagement structure in the lumen of the tube-like stem 54 to manipulate the suture thread without unintentionally catching onto tissue.

It should be appreciated that the needle attachments described herein can be used without the aid of a driver. While a driver may be attached to increase the length of reach or to provide a larger grip, in certain embodiments the function of the needle attachments is not dependent on attaching a driver. In other embodiments, the features of the needle attachments described herein can be incorporated onto a standalone needle tool to perform the same functions without the use of a driver.

Method of Anchoring Soft Tissue to Bone

The present invention includes a method of anchoring a soft tissue to bone. The method may be used for any reconstructive or orthopedic clinical application, including the fastening of ligaments, tendons, muscles, and the like to bone. The method may be used for the repair and reattachment of damaged soft tissue in the shoulder, elbow, wrist, hip, knee, ankle, jaw, and the like.

Figure 9:
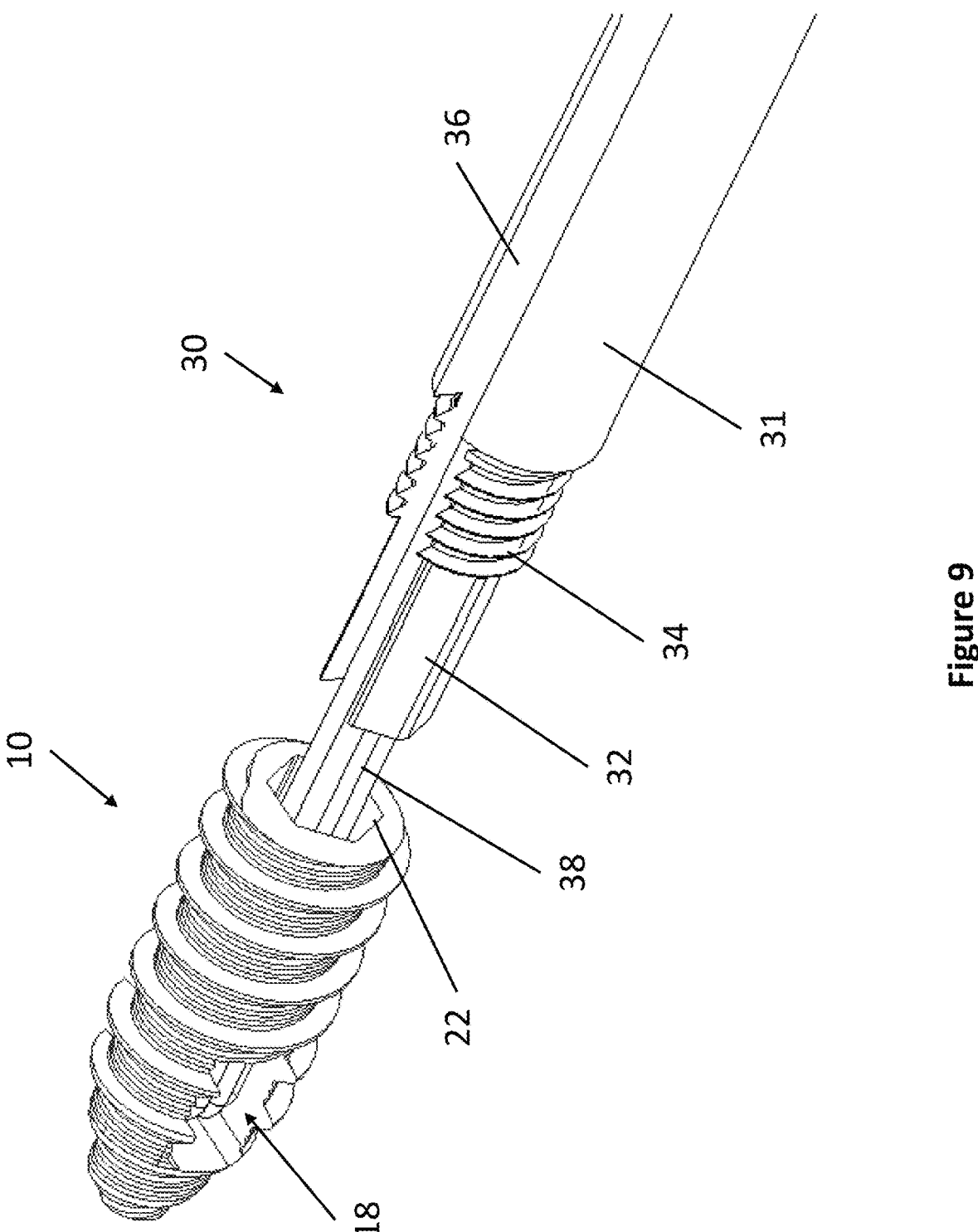
FIG. 9 is a perspective view of the exemplary suture anchor of FIG. 1 being loaded onto the exemplary anchor driver of FIG. 2.
Figure 10:
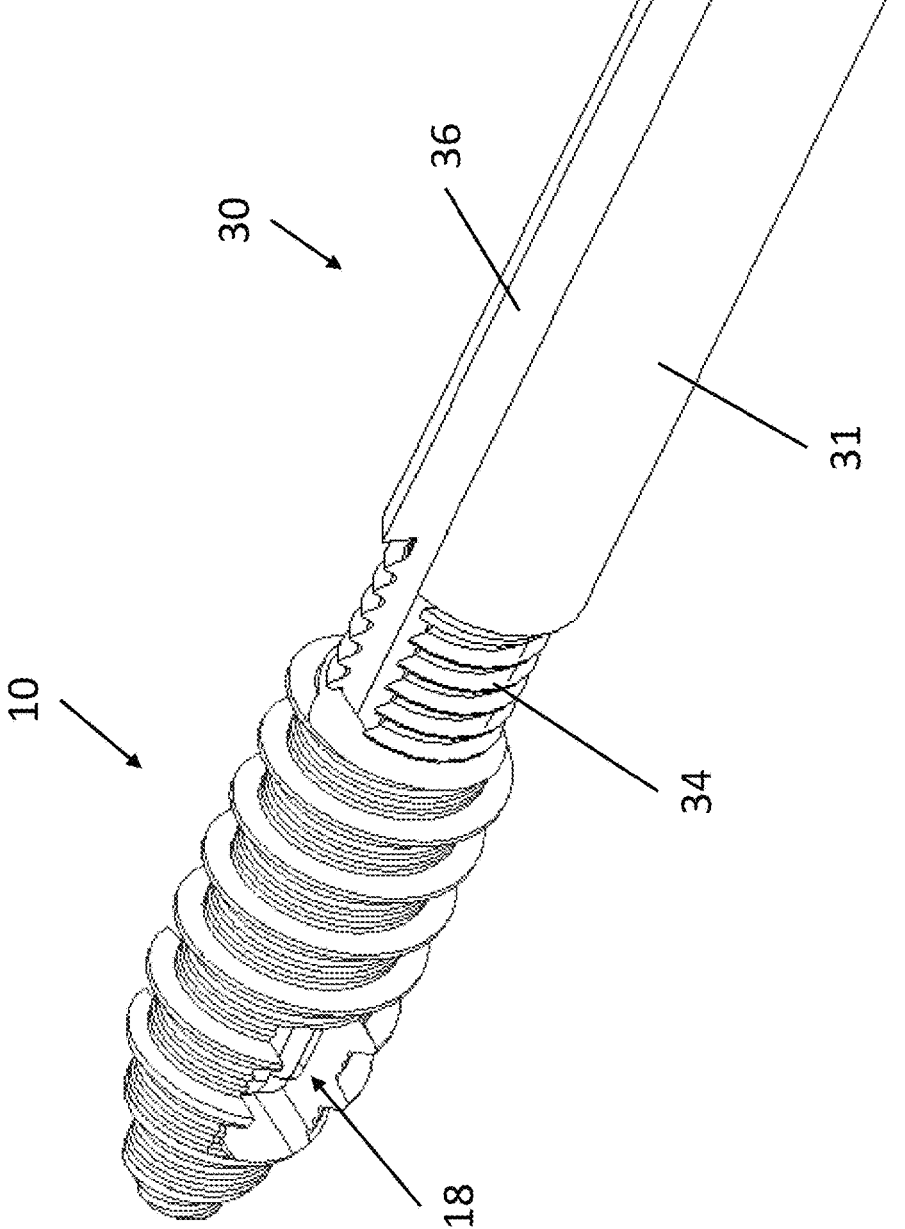
FIG. 10 is a perspective view of the exemplary suture anchor of FIG. 1 loaded onto the exemplary anchor driver of FIG. 2.
Figure 11:
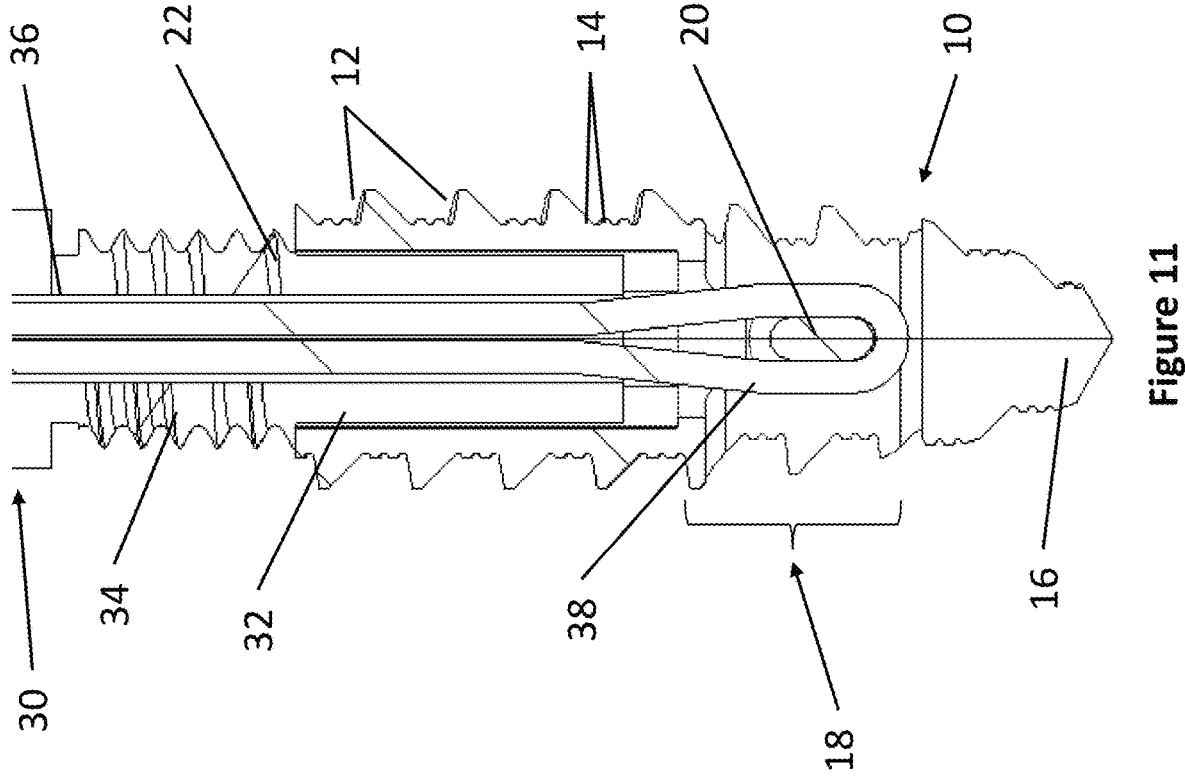
FIG. 11 is a cross-sectional view of the exemplary suture anchor of FIG. 1 loaded onto the exemplary anchor driver of FIG. 2.

Referring now to FIG. 7, a flowchart illustrating an exemplary method 100 of anchoring soft tissue to bone using a needle attachment having a push style engagement structure is depicted. Method 100 begins with step 102 (illustrated in FIGS. 9-11) of loading a suture anchor onto an anchor driver. For example, FIG. 9 depicts an exemplary suture anchor 10 being loaded onto the distal end of an exemplary anchor driver 30. At least one suture 38 is shown secured to suture anchor 10 by passing into driver socket 22, looping around rod 20, and passing out of driver socket 22. The at least one suture 38 is pulled taut through suture channel 36. Driver socket 22 and anchor driving bit 32 may then be mated, as depicted in FIGS. 10 and 11. In one embodiment, the method uses a suture anchor preloaded onto an anchor driver available for immediate use, obviating the need to perform step 102. In other embodiments, the suture anchor is not provided with a preloaded suture.

Figures 12A, 12B, 12C, 12D, 12E, 12F, 12G:
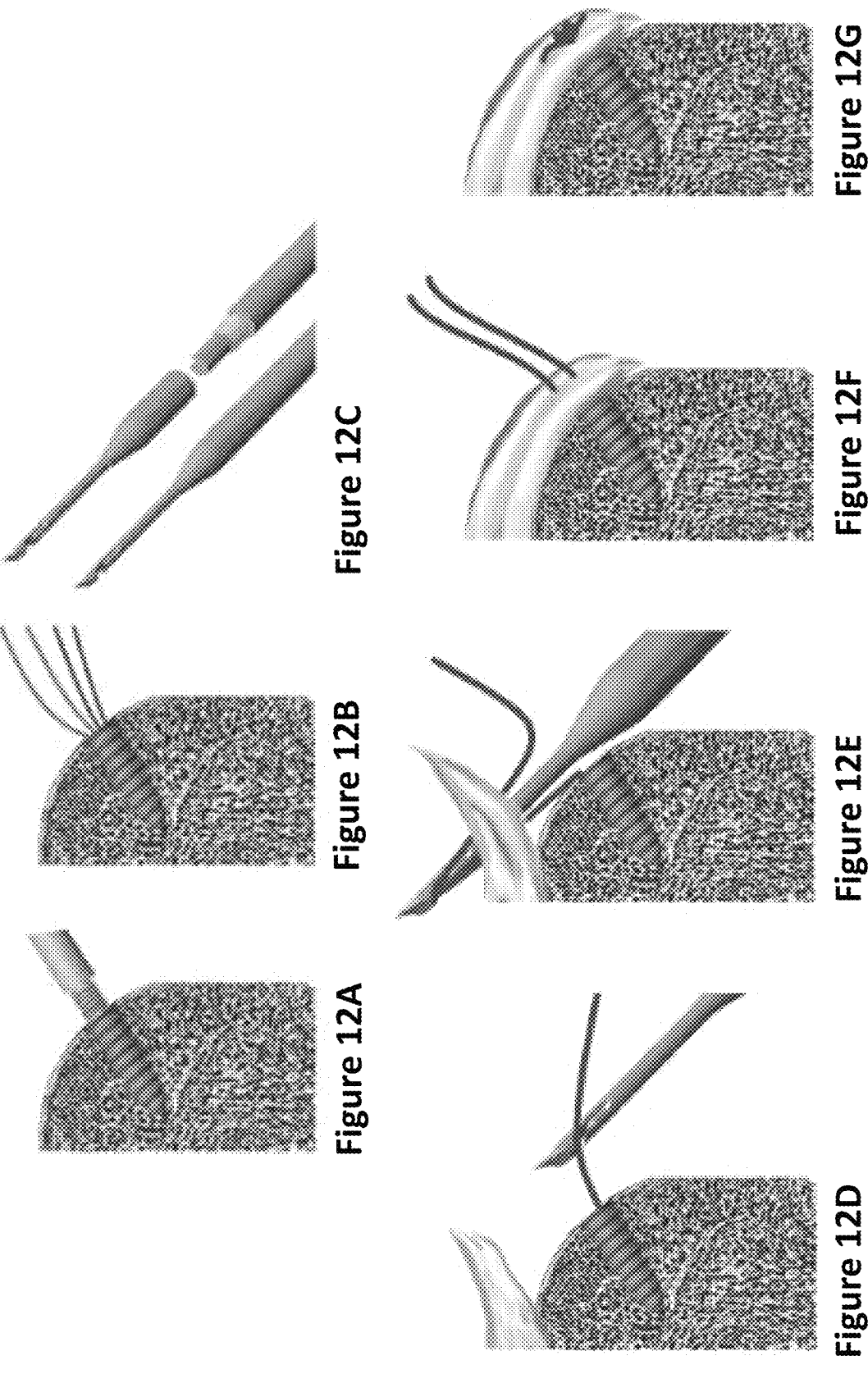
FIG. 12, comprising FIG. 12A through FIG. 12G depicts a series of illustrations showing the steps of the method of FIG. 7.

In step 104 (illustrated in FIG. 12A), the suture anchor is driven into bone with the anchor driver. In one embodiment, the suture anchor is driven into a preformed bore in the bone, which may be formed using a bore-forming tool such as an awl, tap, drill, and the like. In another embodiment, the suture anchor having self-tapping or self-drilling features is driven into the bone without the need for pre-tapping or pre-drilling.

In step 106 (illustrated in FIG. 12B), the suture anchor is disengaged from the anchor driver. Sutures that are attached to the suture anchor are also disengaged from the anchor driver. In embodiments where the suture anchor is not provided with a preloaded suture, a suture is hereby introduced to the suture anchor.

In step 108 (illustrated in FIG. 12C), a needle attachment having a push style engagement structure is joined to the anchor driver.

In step 110 (illustrated in FIG. 12D), a suture is affixed to the needle attachment having a push style engagement structure by affixing the suture to the push style engagement structure.

In step 112 (illustrated in FIG. 12E), the needle attachment with suture is pushed through soft tissue. After pushing through soft tissue, the needle attachment is withdrawn to leave the suture behind.

In step 114 (illustrated in FIG. 12F), the soft tissue is secured against the bone.

In step 116 (illustrated in FIG. 12G), the suture is tied off. For example, the suture ends may be tied together to form a knot. In certain embodiments, the formed knot is pushed to the top surface of the soft tissue, thereby fastening the soft tissue to the bone.

Figure 8:
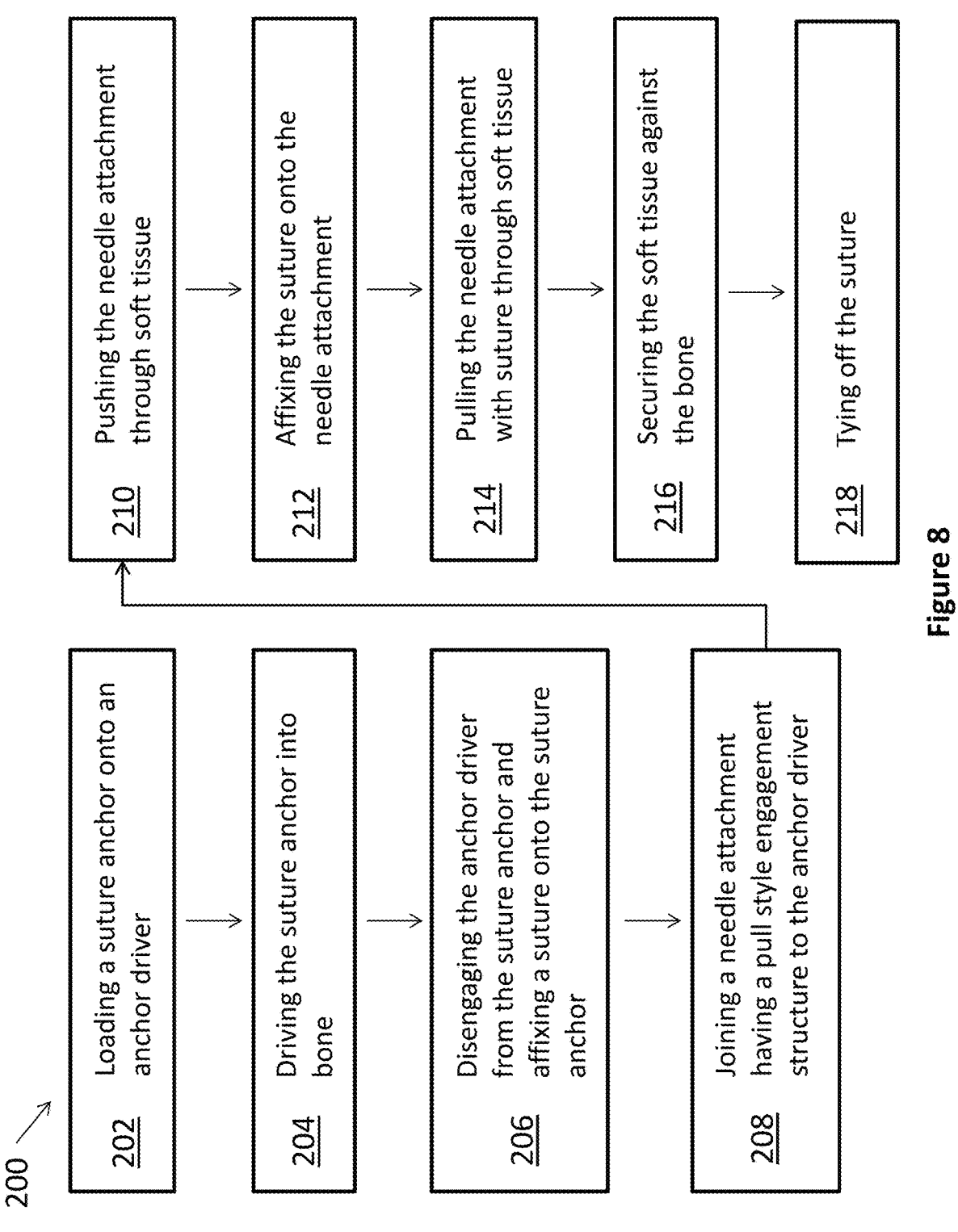
FIG. 8 is a flowchart illustrating an exemplary method for securing soft tissue to bone using the devices of the present invention and a needle attachment having a pull style engagement structure.

Referring now to FIG. 8, a flowchart illustrating an exemplary method 200 of anchoring soft tissue to bone using a needle attachment having a pull style engagement structure is depicted. Method 200 begins with step 202 (illustrated in FIGS. 9-11) of loading a suture anchor onto an anchor driver (as described elsewhere herein). In one embodiment, the method uses a suture anchor preloaded onto an anchor driver available for immediate use, obviating the need to perform step 202. In other embodiments, the suture anchor is not provided with a preloaded suture.

Figures 13A, 13B, 13C, 13D, 13E, 13F, 13G, 13H:
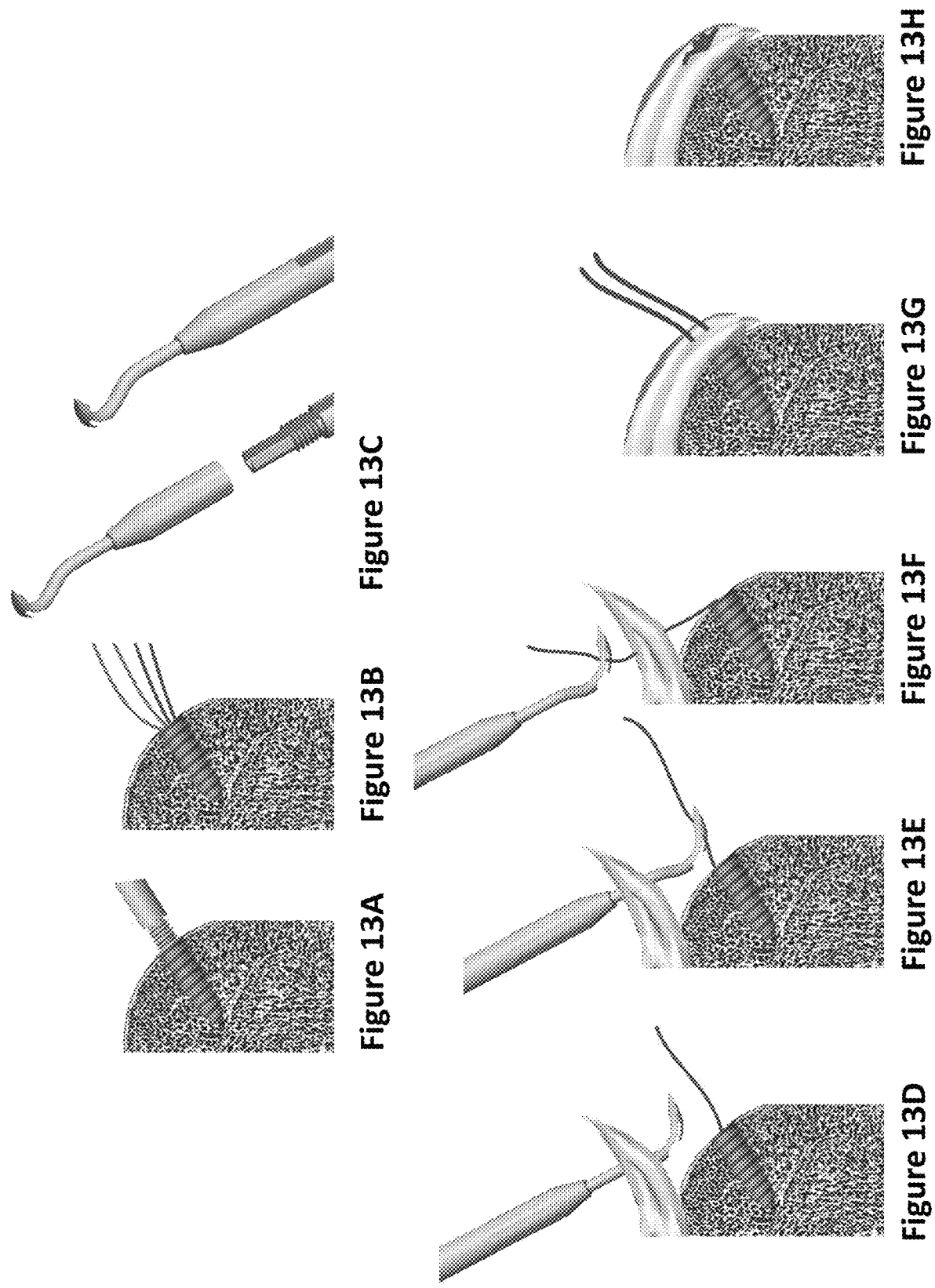
FIG. 13, comprising FIG. 13A through FIG. 13H depicts a series of illustrations showing the steps of the method of FIG. 8.

In step 204 (illustrated in FIG. 13A), the suture anchor is driven into bone with the anchor driver. In one embodiment, the suture anchor is driven into a preformed bore in the bone, which may be formed using a bore-forming tool such as an awl, tap, drill, and the like. In another embodiment, the suture anchor having self-tapping or self-drilling features is driven into the bone without the need for pre-tapping or pre-drilling.

In step 206 (illustrated in FIG. 13B), the suture anchor is disengaged from the anchor driver. Sutures that are attached to the suture anchor are also disengaged from the anchor driver. In embodiments where the suture anchor is not provided with a preloaded suture, a suture is hereby introduced to the suture anchor.

In step 208 (illustrated in FIG. 13C), a needle attachment having a pull style engagement structure is joined to the anchor driver.

In step 210 (illustrated in FIG. 13D), the needle attachment is pushed through soft tissue.

In step 212 (illustrated in FIG. 13E), a suture is affixed to the needle attachment having a pull style engagement structure by affixing the suture to the pull style engagement structure.

In step 214 (illustrated in FIG. 13F), the needle attachment with suture is pulled through soft tissue. After pulling through soft tissue, the needle attachment is withdrawn to leave the suture behind.

In step 216 (illustrated in FIG. 13G), the soft tissue is secured against the bone.

In step 218 (illustrated in FIG. 13H), the suture is tied off. For example, the suture ends may be tied together to form a knot. In certain embodiments, the formed knot is pushed to the top surface of the soft tissue, thereby fastening the soft tissue to the bone.

In certain embodiments, the method comprises using one or more of the suture anchors of the invention for fastening the soft tissue at one or more locations along the bone. The number and spacing of the anchors may be varied depending on the particular application and extent of the injury.

Kit for Securing Soft Tissue to Bone

The present invention relates to a kit comprising components useful within the methods of the invention and instructional material that describes, for instance, the method of securing soft tissue to bone as described elsewhere herein. The kit may comprise components and materials useful for performing the methods of the invention. For instance, the kit may comprise suture anchors and anchor drivers of the present invention.

In one embodiment, the kit comprises at least one suture anchor comprising at least one major thread and at least two microthreads, wherein the at least one major thread has a larger major diameter than the at least two microthreads. In one embodiment, the system comprises an anchor driver capable of accepting various attachments at its distal end such that an operator can change the functionality of the driver based on the type of attachment in use. For example, one attachment may be a needle attachment having a notch for passing sutures through soft tissue. The system may further comprise one or more additional attachments for manipulating the soft tissue or bone or to form a knot using the passed sutures. In certain embodiments, the kit comprises at least one suture anchor preloaded onto an anchor driver.

In certain embodiments, the kit comprises instructional material. Instructional material may include a publication, a recording, a diagram, or any other medium of expression which can be used to communicate the usefulness of the device or kit described herein. The instructional material of the kit of the invention may, for example, be affixed to a package which contains one or more instruments which may be necessary for the desired procedure. Alternatively, the instructional material may be shipped separately from the package, or may be accessible electronically via a communications network, such as the Internet.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A suture anchor, comprising:

an elongate anchor body having a proximal end, a distal end and a length therebetween;

at least one major thread covering the length of the anchor body, wherein the at least one major thread has a major diameter between 2 mm and 10 mm and a thread pitch between 0.1 mm and 5 mm; and at least two minor threads covering the length of the anchor body, wherein the at least two minor threads occupy a space between the at least one major thread, wherein the at least two minor threads have major diameters between 1 mm and 9 mm and thread pitches between 0.1 mm and 5 mm, and wherein the major diameters of the at least two minor threads are smaller than the major diameters of the at least one major thread;

wherein the at least one major thread has a first angular profile comprising a proximal major thread face and a distal major thread face, wherein the proximal major thread face extends substantially planar at a first angle from a root of the anchor with a longitudinal axis of the elongated body, wherein the distal major thread face extends substantially planar from a root of the anchor and makes a second angle less than 90 degree with the longitudinal axis, and wherein the first angle is closer to perpendicular with the longitudinal axis than the second angle;

wherein each of the at least two minor threads have a second angular profile comprising a proximal minor thread face and a distal minor thread face, wherein the proximal minor thread faces makes a non-perpendicular angle less than 90 degrees with the longitudinal axis and the distal minor thread faces makes a non-perpendicular angle less than 90 degrees with the longitudinal axis; and wherein the first and second angular profiles are different along the length, and wherein the at least two minor threads extend to their major diameter in the second angular profile distal from where the at least one major thread extends to its major diameter in the first angular profile.

2. The suture anchor of claim 1, further comprising at least one suture secured to the anchor body.

3. The suture anchor of claim 1, wherein the proximal end of the anchor body comprises a channel for engagement with an installation tool.

4. The suture anchor of claim 3, wherein at least one suture is secured within the channel of the anchor body.

5. The suture anchor of claim 3, wherein the channel is surrounded by the major thread and the at least two minor threads along an entire length of the channel.

6. The suture anchor of claim 5, wherein the channel terminates proximally at a proximal face of the elongate body, and wherein the major thread terminates proximally at the proximal face.

7. The suture anchor claim 6, wherein a root diameter of the elongate anchor body is constant from the proximal face to a distal portion of the elongate body.

8. The suture anchor claim 7, wherein the major thread diameter is constant along the channel and extending to a distal portion of the elongate body.

9. The suture anchor of claim 1, wherein the major diameter of the at least one major thread decreases along at least a portion of the anchor body length in a direction towards a distal tip.

10. The suture anchor of claim 1, wherein the suture anchor further comprises an aperture positioned along the length of the elongate anchor body and passes laterally through the elongate anchor body and wherein the aperture comprises a rod that extends across the aperture and is configured to secure a length of suture looped around the rod.

11. The suture anchor of claim 1, wherein each adjacent thread of the at least one major thread and at least two minor threads are positioned to abut each other.

12. A suture anchor, comprising:

an elongate anchor body having a proximal end, a distal end and a length therebetween;

at least one major thread having a major diameter, the at least one major thread covering the length of the anchor body; and at least one minor thread having a major diameter smaller than the major diameter of the at least one major thread, the at least one minor thread covering the length of the anchor body, wherein the at least one major thread has a first angular profile comprising a proximal major thread face and a distal major thread face, wherein the proximal major thread face extends substantially planar at a first angle from a root of the anchor with a longitudinal axis of the elongated body, wherein the distal major thread face extends substantially planar from a root of the anchor and makes a second angle less than 90 degree with the longitudinal axis, and wherein the first angle is closer to perpendicular with the longitudinal axis than the second angle, wherein the major diameter of the at least one major thread decreases along at least a portion of its length in a direction towards a distal tip, while the major diameter of the at least one minor thread remains constant along the portion of its length;

wherein the at least one minor thread has a second angular profile comprising a proximal minor thread face and a distal minor thread face, wherein the proximal minor thread faces make a non-perpendicular angle less than 90 degrees with the longitudinal axis and the distal minor thread faces make a non-perpendicular angle less than 90 degrees with the longitudinal axis; and wherein the first and second angular profiles are different along the length, and wherein the at least one minor thread extend to its major diameter in the second angular profile distal from where the at least one major thread extends to its major diameter in the first angular profile.

13. The suture anchor of claim 12, further comprising at least one suture secured to the anchor body.

14. The suture anchor of claim 12, wherein the proximal end of the anchor body comprises a channel for engagement with an installation tool.

15. The suture anchor of claim 14, wherein at least one suture is secured within the channel of the anchor body.

16. The suture anchor of claim 14, wherein the channel is surrounded by the major thread and the at least two minor threads along an entire length of the channel.

17. The suture anchor of claim 16, wherein the channel terminates proximally at a proximal face of the elongate body, and wherein the major thread terminates proximally at the proximal face.

18. The suture anchor claim 17, wherein a root diameter of the elongate anchor body is constant from the proximal face to a distal portion of the elongate body.

19. The suture anchor claim 18, wherein the major thread diameter is constant along the channel and extending to a distal portion of the elongate body.

20. The suture anchor of claim 12, wherein the major diameter of the at least one major thread decreases along at least a portion of the anchor body length in a direction towards a distal tip.

21. The suture anchor of claim 12, wherein the suture anchor further comprises an aperture positioned along the length of the elongate anchor body and passes laterally through the elongate anchor body and wherein the aperture comprises a rod that extends across the aperture and is configured to secure a length of suture looped around the rod.

22. The suture anchor of claim 12, wherein each adjacent thread of the at least one major thread and at least two minor threads are positioned to abut each other.

23. The suture anchor of claim 12, wherein the at least one minor thread occupies the space between the at least one major thread such that there is no surface between adjacent threads along a longitudinal axis of the length of the anchor body.

* * * * *